United States Patent
Wilford (10) Patent No.: US 11,850,183 B2
(45) Date of Patent: Dec. 26, 2023

(54) HEAD WRAP

(71) Applicant: Michael L. Wilford, Chicago, IL (US)

(72) Inventor: Michael L. Wilford, Chicago, IL (US)

( * ) Notice: Subject to any disclaimer, the term of this patent is extended or adjusted under 35 U.S.C. 154(b) by 613 days.

(21) Appl. No.: 16/986,479

(22) Filed: Aug. 6, 2020

(65) Prior Publication Data

US 2021/0052419 A1 Feb. 25, 2021

Related U.S. Application Data

(60) Provisional application No. 62/889,391, filed on Aug. 20, 2019.

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0002* (2013.01); *A61F 2007/0052* (2013.01); *A61F 2007/0231* (2013.01); *A61F 2007/0244* (2013.01)

(58) Field of Classification Search
CPC ...... A61F 2007/0002; A61F 2007/0052; A61F 2007/0054; A61F 2007/0231; A61F 2007/0244; A61F 7/0085; A61F 7/02
See application file for complete search history.

(56) References Cited

U.S. PATENT DOCUMENTS

| | | | |
|---|---|---|---|
| 4,225,989 A | 10/1980 | Corbett et al. | |
| 4,765,338 A | 8/1988 | Turner et al. | |
| 5,169,384 A | 12/1992 | Bosniak et al. | |
| 5,228,431 A | 7/1993 | Giarretto | |
| 5,342,411 A | 8/1994 | Maxted et al. | |
| 5,437,610 A | 8/1995 | Cariapa et al. | |
| 5,466,250 A | 11/1995 | Johnson, Jr. et al. | |
| 5,584,798 A | 12/1996 | Fox | |
| 5,603,728 A | 2/1997 | Pachys | |
| 5,733,321 A | 3/1998 | Brink | |
| 5,865,841 A | 2/1999 | Kolen et al. | |
| 5,894,615 A | 4/1999 | Alexander | |
| 5,925,010 A | 7/1999 | Caprio, Jr. | |
| 5,950,234 A | 9/1999 | Leong et al. | |

(Continued)

FOREIGN PATENT DOCUMENTS

| GB | 2417423 | 3/2006 |
|---|---|---|
| JP | 200542261 | 2/2005 |

(Continued)

*Primary Examiner* — Tigist S Demie
(74) *Attorney, Agent, or Firm* — Aronberg, Goldgehn, Davis, & Garmisa (57) ABSTRACT

The subject matter of the invention relates to therapy wraps for the application of compression and thermal therapy to a patient by fluid pumped through the wrap. The wraps are formed of at least two layers of material which are sealed together to form at least one cavity between them. At least two layers of the wrap are sealed together using a plurality of different seal patterns. The unique shape of the wrap and placement of the seals provides a wrap that may be folded to fit a patient's head and circulate fluid in a manner to compress the wrap against the wearer's head, particularly in areas where hair growth is desired while avoiding the application of therapy to other areas of the head, particularly the forehead and ears.

19 Claims, 9 Drawing Sheets

(56) References Cited

U.S. PATENT DOCUMENTS

| | | |
|---|---|---|
| 5,989,285 A | 11/1999 | DeVilbiss et al. |
| 6,080,120 A | 6/2000 | Sandman et al. |
| 6,126,680 A | 10/2000 | Wass |
| 6,178,562 B1 | 1/2001 | Elkins |
| 6,183,501 B1 | 2/2001 | Latham |
| 6,277,143 B1 | 8/2001 | Klatz et al. |
| 6,290,662 B1 | 9/2001 | Morris et al. |
| 6,312,453 B1 | 11/2001 | Stefanile et al. |
| 6,352,550 B1 | 3/2002 | Gildersleeve |
| 6,440,093 B1 | 8/2002 | McEwen et al. |
| 6,530,941 B1 | 3/2003 | Muller et al. |
| 6,551,347 B1 | 4/2003 | Elkins |
| 6,610,084 B1 | 8/2003 | Torres |
| 6,736,787 B1 | 5/2004 | McEwen et al. |
| 7,198,093 B1 | 4/2007 | Elkins |
| 7,207,959 B1 | 4/2007 | Chandran |
| 7,211,104 B2 | 5/2007 | Edelman |
| 7,354,410 B2 | 4/2008 | Perry et al. |
| 7,396,345 B2 | 7/2008 | Knighton et al. |
| 7,442,175 B2 | 10/2008 | Meyer et al. |
| 7,896,910 B2 | 3/2011 | Schirrmacher et al. |
| 8,096,964 B1 * | 1/2012 | Bruehwiler ............ A61F 13/085 602/23 |
| 9,101,463 B2 | 8/2015 | Stormby |
| 9,132,057 B2 | 9/2015 | Wilford et al. |
| 2002/0058976 A1 | 5/2002 | Lee |
| 2004/0249427 A1 | 12/2004 | Nabilsi |
| 2005/0070828 A1 | 3/2005 | Hampson et al. |
| 2005/0107855 A1 | 5/2005 | Lennox et al. |
| 2005/0143797 A1 | 6/2005 | Parish et al. |
| 2008/0058911 A1 | 3/2008 | Parish et al. |
| 2008/0228248 A1 | 9/2008 | Guyuron et al. |
| 2009/0069731 A1 | 3/2009 | Parish et al. |
| 2010/0210982 A1 | 9/2010 | Balachandran et al. |
| 2012/0130457 A1 | 5/2012 | Gammons et al. |
| 2012/0172774 A1 | 7/2012 | Lowe et al. |
| 2013/0138185 A1 | 5/2013 | Paxman et al. |
| 2014/0046410 A1 | 2/2014 | Wyatt |
| 2016/0317348 A1 | 11/2016 | Banker |
| 2016/0346115 A1 * | 12/2016 | Varga ........................ A61F 7/02 |
| 2017/0239082 A1 | 8/2017 | Unver et al. |
| 2018/0005571 A1 | 3/2018 | Quisenberry et al. |
| 2020/0046597 A1 | 2/2020 | Quisenberry et al. |

FOREIGN PATENT DOCUMENTS

| | | |
|---|---|---|
| JP | 2005042261 | 2/2005 |
| WO | WO-01/62193 | 8/2001 |

* cited by examiner

HEAD WRAP

BACKGROUND

The present apparatus relates generally to fluid filled wraps for applying thermal therapy to a patient's head as well as applying compression without the need for additional air compression systems. In practice, the wraps are connected to a fluid circulating machine that supplies a thermal fluid to the wrap through tubes connecting the machine and the wrap. Generally, a thermal transfer fluid may be circulated through the wrap and machine by pumping fluid that has been heated or cooled by the machine from a reservoir in the machine through a tube connected to a wrap, circulating the fluid through the wrap, and allowing the fluid to exit the wrap through another tube which returns the fluid to the machine. An example of a suitable machine for circulating fluid is described in U.S. Pat. No. 8,979,915 filed on behalf of Wilford et al., the entirety of which is incorporated herein by reference.

More particularly, the present apparatus is directed to a removable wrap that is foldable to accommodate the contours of a human head. While other wraps are known (see, e.g. U.S. Pat. Nos. 9,132,057, 9,962,285, 9,931,240, and 9,510,994, the entireties of which are incorporated herein for all purposes), prior wraps are not particularly shaped such that they can be properly applied to the human head when folded. Prior known shapes of wraps tend to kink, block fluid flow, unnecessarily overlap portions of the wrap, and do not adequately flow fluid through the wrap with sufficient pressure. The wraps include at least one fluid-tight chamber allowing for the ingress and egress of a fluid. Layers of the wrap are sealed together about an outer perimeter and at multiple locations, particularly within a fluid chamber. The seals are arranged in patterns to form fluid pathways, and the size and location of the seals are varied so as to create multiple zones having differing seal patterns and thus differing fluid pathways.

Compression and thermal wraps similar to the invention described herein have been in use for many years. For example, wraps constructed from multiple layers of fluid tight material and exhibiting fluid chambers having dot seal patterns are described in U.S. Patent Application Publication No. 2014/0012169 filed on behalf of Wilford et al., the entirety of which is incorporated herein by reference. The wraps are designed to be applied an area of the patient's body where therapy is desired. Once in place, a fluid (either a gas or a liquid) is forced into a fluid-tight chamber of the wrap thereby applying therapy to the portion of the patient's body contacted by the wrap. Adapting a fluid wrap that folds to fit a human head presents unique challenges because the head is round and hard and because the head does not provide for convenient ways in which to secure the wrap to the head. The round shape of the head makes it difficult to form a flat wrap to the scalp by folding while also preventing the wrap from kinking and blocking fluid flow.

As described in detail below, the present invention provides a unique solution to the aforementioned problems.

SUMMARY OF EMBODIMENTS

The present therapy wraps are formed having a plurality of differing seal pattern zones in layers of material that are then folded to create a cap for a human head. The wraps may be constructed of two or more layers of material which are sealed together to from a fluid tight cavity bounded by a cavity seal. Additionally, at least one hose is provided such that one end of the hose is in fluid communication with the interior of the cavity while the other end of the hose is in fluid communication with the environment. The hose may be provided with various valves to assist in the control of fluid moving from the environment into or out of the interior of the cavity.

To prevent kinking, one or more zones of a first, large internal seal pattern may be created around the locations in the fluid chamber where kinking occurs, such as around the fluid tubes and at various locations where the wrap is folded to better fit the head. The zones in those areas are provided with a pattern that is has comparatively large distances between each seal with respect to the seal pattern or patterns surrounding the perimeters of the zones. The area surrounding the perimeter of the zones, and preferably the area constituting the balance of the wrap, is provided with a small seal pattern, where the distance between the seals forming the small seal pattern are less than distances between the seals contained in the large seal pattern zones. The smaller pattern decreases the overall internal volume of the wrap, thereby limiting the total amount of fluid that can enter the wrap at a given time, while the large pattern zones ensure continuous fluid flow by providing larger pathways in critical areas and preventing kinking in those areas. Limiting the amount of fluid decreases the weight of the wrap when filled and reduces the thermal load on the thermal therapy device heating or cooling the liquid for the wrap. That allows the thermal therapy device to more rapidly heat or cool the liquid, and hence wrap, thereby performing more efficiently and ensuring more reliable therapy. In one embodiment, the wrap is provided with a circuitous path that forces inflowing fluid to encircle the wearer's head before filling the balance of the wrap with fluid. By encircling the wearer's head first, the fluid assists in cinching the wrap to the wearer's head before completely filling, and thus the wrap is prevented from pushing away from the head or becoming dislodged due to uneven fluid dispersion as the wrap fills.

The wraps constructed according to various embodiments may be used to apply compression and thermal therapy to a body. It is contemplated that the wraps could be used to apply such therapy by using the wraps in conjunction with a therapy machine such as the device disclosed in U.S. Pat. No. 8,979,915. That device is equipped with a number of ports which may be connected to the hose or hoses of the wraps discussed herein. The device provides fluid in the form of a thermal liquid through the hoses connected to the ports and into the wraps in order to provide thermal and compression therapy. It should be noted that the present embodiments of the wrap do not include a chamber for gas or air compression. It was found that the application of air compression tended to cause the wrap to pull away from the head and scalp. Additionally, through the unique design of the fluid chambers and seal patterns of the present system, adequate compression of the wrap against the head can be achieved through the use of fluid (that is, a thermal liquid) that is cycled through the wrap. Specific embodiments of various shapes of the wrap and the locations of preferred pattern zones are set forth in more detail below.

DETAILED DESCRIPTION OF EMBODIMENTS

Throughout the specification, wherever practicable, like structures will be identified by like reference numbers.

It is preferable that the therapy system described herein is used to apply thermal therapy or thermal and compression therapy utilizing various specially designed wraps. The particular shape and benefits afforded by the various specially designed wraps for use with the therapy system will be described in detail below. The wraps may be constructed for the application of thermal treatment or thermal and compression therapy using a circulated heated or cooled fluid. The therapy wraps may be constructed utilizing at least two layers of material and at least two hoses. The two or more layers of material and two or more hoses are laminated together at least about the perimeter of the two layers of material thereby forming a cavity between at least two or more layers such that the two hoses provide pathways for the ingress and egress of fluid to and from the cavity.

The basic construction of the embodiments is essentially the same. Each wrap includes at least two fluid tight layers of material and at least two hoses. The two or more layers of material and at least two hoses are sealed together, for example using radio frequency (RF) welding, so as to create a fluid tight chamber between them such that fluid is permitted ingress to and egress from the chamber by way of the hoses. Material suitable for constructing wraps include 200 Denier nylon oxford laminated to urethane for use in creating the exterior layers where the urethane may be sealed together with the nylon laminate facing outward. Such material may be purchased from a variety of companies including American National Manufacturing of 252 Mariah Cir, Corona, CA 92879. However, in one embodiment, only one of the layers may include the nylon laminate while the other is constructed of only urethane (or urethane laminated with a material that is more elastic than nylon). Alternately, the exterior of the wrap may include nylon while the interior portion of the wrap corresponding to the shape of the fluid chamber is constructed only of urethane. In such embodiments, when the wrap is folded and fitted to the head, the nylon layer faces outward, while the more elastic layer, facing inward, is placed against the scalp. That allows the fluid chamber of the wrap to more readily expand against the scalp as the relatively inelastic nylon layer constricts the outer layer from expanding while the more elastic inner layer corresponding to the fluid chamber expands to accommodate the influx of fluid.

It should be understood that the hoses referred to herein are in the simplest sense pieces of conduit that provide an access pathway from the exterior of a fluid tight cavity (or fluid chamber) to the interior of the fluid tight cavity. A hose may be of more complex design however, such as a multiple pieces of conduit having one or more valves or connection pieces all coupled together which essentially provide the same pathway between the exterior and interior of the fluid tight cavity. Preferably, the hose is simply a tube which provides the pathway between the interior of the cavity and the exterior of the cavity by traversing the seal between the layers of material which define the fluid tight cavity. However, the hose could alternatively be a port which is formed in the sidewall of the fluid tight cavity to which another hose may be connected.

In the preferred construction of each of the wraps recited below, a first sheet of urethane is provided having at least one side coated with nylon. The nylon may be coated on the outside of the layer intended to have contact with the skin so as to provide a barrier between the skin and urethane and to provide structural integrity for the wrap. The nylon side is placed face down such that the urethane side is facing up. Two hoses are place on top of the first sheet such that the hoses each cross over the perimeter of the first sheet and thus a first end of a first hose and a first end of a second hose each rest on top of the first sheet. The second end of the first hose and the second end of the second hose are each oriented such that each is in contact with the open air. Preferably, the hoses are oriented such that the longitudinal axis of each hose aligns perpendicularly to the perimeter of the first sheet at the point at which each hose crosses the perimeter of the first sheet. A second sheet of urethane material of substantially the same size and shape as the first sheet is oriented over the first sheet and laid on top of the first sheet such that the perimeters of both the first and second sheets substantially align. The second sheet thus substantially covers the first sheet and covers the first end of the first hose and the first end of the second hose.

The sheets may then be sealed together, preferably about their perimeters. The seal is formed such that the first and second sheets are sealed together thereby creating a cavity between the first and second sheet where the first and second hoses are sealed between the first and second sheets such that first end of the first hose and the first end of the second hose communicate with the cavity between the first and second sheets. Because the first end of the first hose and the first end of the second hose communicate with the cavity and the second end of the first hose and the second end of the second hose communicate with the open air, fluid may be passed through the first or second hose to either fill or drain the cavity. The seal forming the cavity further surrounds the exterior of the first and second hoses such that the only avenue for fluid to ingress to and egress from the cavity is through the first or second hoses. The wraps may also include fasteners, such as hook and loop, snaps, buttons, eyelets or other type of fasteners. It should be apparent that while it is preferable that the at least two layers of material are sealed together such that only one seal is necessary to form the cavity and connect the layers of material together, multiple seals could be utilized.

With respect to the wrap designs detailed herein, the wraps may be made of a single cavity and may be provided with various seal patterns and pathways described herein. Bearing in mind the aforementioned general construction of the wraps, a number of specially designed wraps will now be described with reference to the Figures.

Figure 1A:
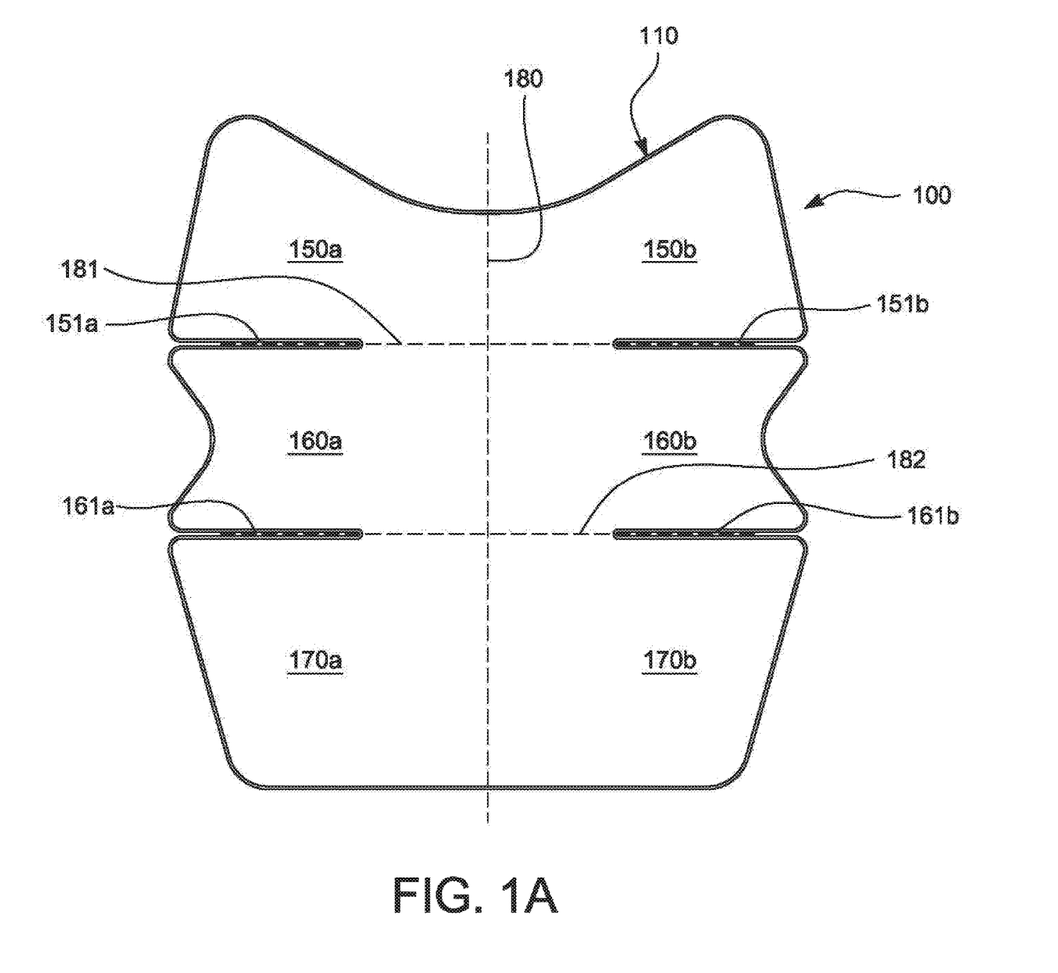
FIG. 1A is a plan view of an embodiment of a wrap laid flat.
Figure 1B:
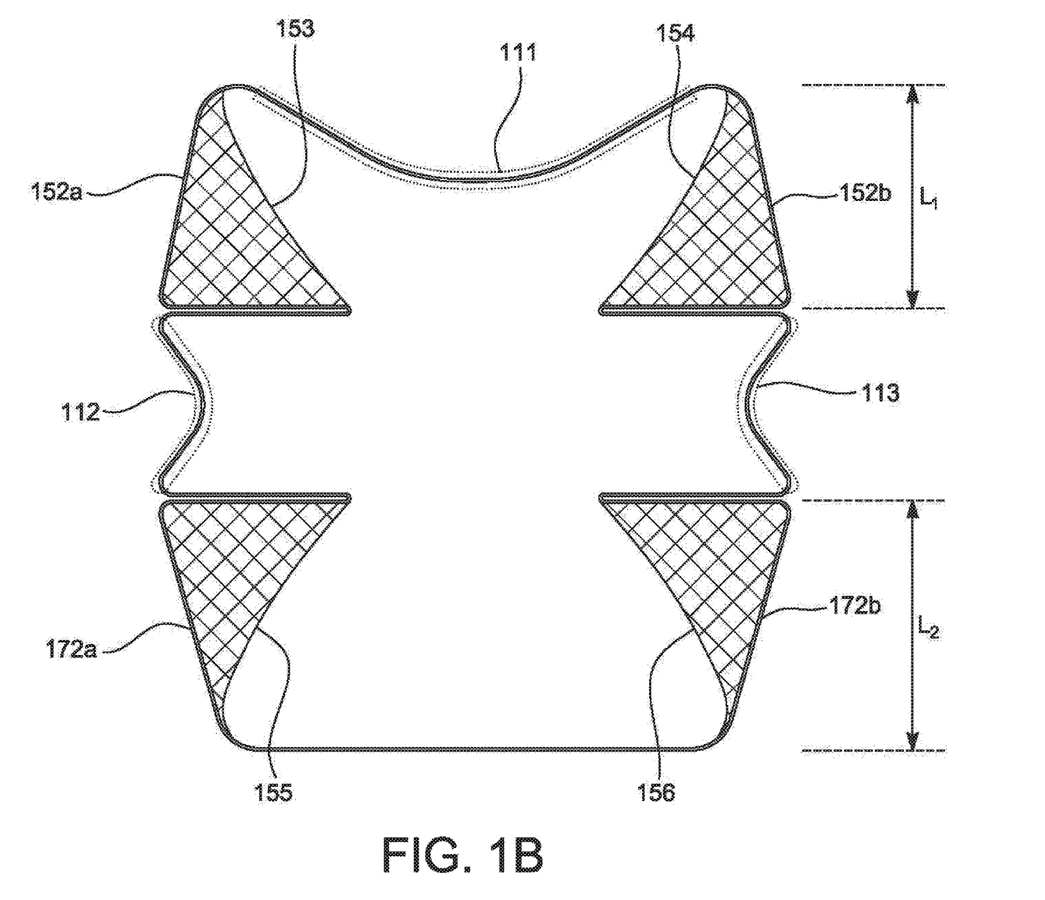
FIG. 1B is a plan view of an embodiment of a wrap laid flat and depicting void areas.

Referring now to FIG. 1A, a wrap generally having a contoured shape is identified as 100. The wrap in FIG. 1A is constructed using two layers of material, all sealed together about perimeter 110. The perimeter seal 110 seals together the two layers to form a cavity there between. Additional seals may be added to modify the shape of the cavity. For example, in FIG. 1B, seals 153, 154, 155, and 156 are formed to reduce the size of the cavity such that the cavity does not extend all the way to the perimeter seal 110 in all areas. In the embodiment of FIG. 1B, the cavity restricting seals 153, 154, 155 extend from the perimeters of the lobes to the slits thereby cutting off a portion of the cavity within of each lobes 150*a*, 150*b*, 170*a*, and 170*b*, respectively. It should be understood that the various seals may overlap and that additional layers and cavities could be added. In forming the wrap, a first layer of material is supplied, hoses, 191 and 192 (see FIG. 3) are supplied and a second layer of material is supplied on top of the first layer. The first and second layers of material are sealed together about their perimeter so as to form a cavity between them where fluid may ingress to and egress from the cavity only by way of hoses 191 and 192.

The overall shape of the cavity of the wrap depicted in FIGS. 1A-1B can generally be described as having six lobes that are symmetrical about a longitudinal axis, the length of the wrap being greater than the width. The shape includes two front lobes 150*a* and 150*b*, two middle lobes 160*a* and 160*b* and two back lobes 170*a* and 170*b*. Dashed lines 180, 181, and 182 generally depict the dividing lines between the various lobes. It should be appreciated that the other wrap design described in FIG. 2A exhibits the same general construction where the shape includes two front lobes 250*a* and 250*b*, two middle lobes 260*a* and 260*b* and two back lobes 270*a* and 270*b*. Dashed lines 280, 281, and 282 generally depict the dividing lines between the various lobes. As shown in FIG. 1A, the top two lobes 150*a* and 150*b* are mirror images of each other reflected about the dividing line 180 and form the top third of the wrap. Similarly the middle two lobes 160*a* and 160*b* are mirror images of each other reflected about the dividing line 180 and form the middle third. The bottom two lobes 170*a* and 170*b* are mirror images of each other reflected about the dividing line 180 and form the bottom third of the wrap. Thus, dashed line 180 forms a vertical central axis line whether the right half and left half of the wrap are symmetrical about line 180.

Figure 6:
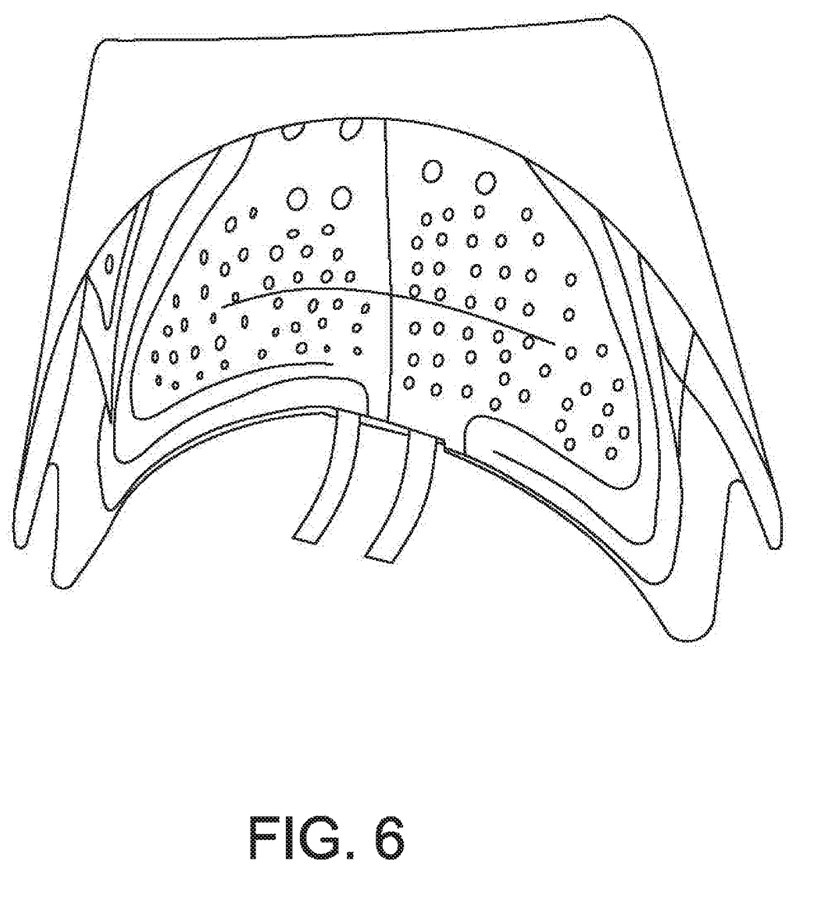
FIG. 6 is a perspective view of an embodiment of a wrap in a folded state.
Figure 7:
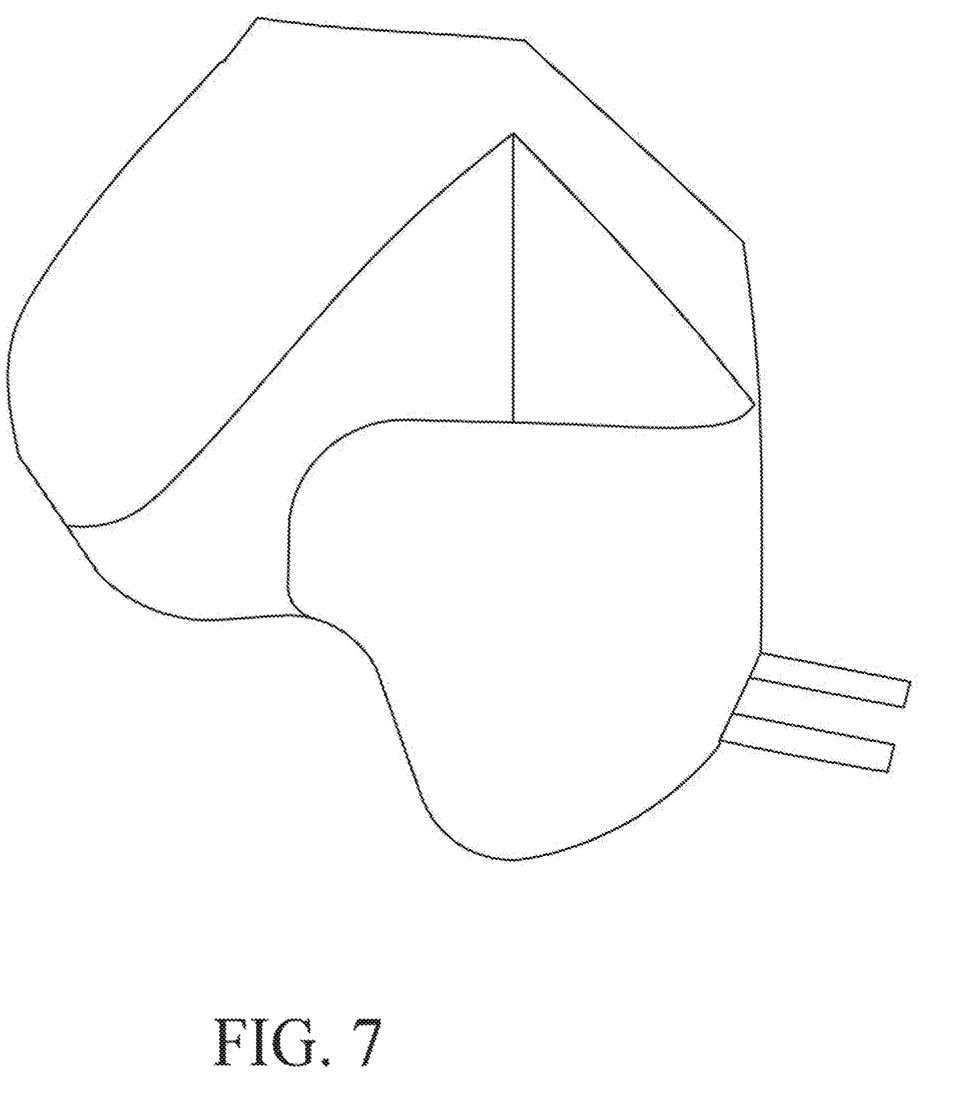
FIG. 7 is a perspective view of an embodiment of a wrap in a folded state.

As shown in FIG. 1A, slit 151*a* partially separates lobe 150*a* from 160*a*, slit 151*b* partially separates lobe 150*b* from 160*b*, slit 161*a* partially separates lobe 160*a* from 170*a* and slit 161*b* partially separates lobe 160*b* from lobe 170*b*. As shown in FIGS. 6 and 7, the slits allow the lobes to be folded over one another to create a three-dimensional cap that accommodates a person's head.

The perimeter seal 110 shapes the outer perimeter of the lobes to contour the lobes in such a way that the lobes provide specific wrap coverage for a person's head when the wrap is folded. In FIG. 1B, some of the seals have been encircled in dotted lines to exaggerate the seals for explanatory purposes. For example, arched seal 111 (which is part of the perimeter seal 110) is curves, or parabolic, and conforms generally to the hairline of a patient and arches over the eyes and forehead. As shown in FIG. 1A, the parabolic curve is concave as it extends into the area of the wrap. The shape allows the thermal cavity of the wrap to better conform to the scalp treatment area where maintenance of hair growth is desired rather that traversing the forehead of a patient where therapy is unnecessary and undesirable. Seals 112 and 113 are each curved, or parabolic seals that curve around a patient's ears. The ears may be particularly sensitive to cold and therefore it is desirable that the wrap avoid applying thermal therapy to the ears. However, the hairline dips below the top of the ear. By curving seals 112 and 113, the wrap is able to fit close to the scalp, along the hairline but between the tops of the ears and the scalp to apply thermal therapy to where maintenance of hair growth is desired while leaving the ears uncovered.

The cavity seals 153, 154, 155, and 156 join with the perimeter seal 110 to create void areas 152*a*, 152*b*, 172*a* and 172*b* in lobes 150*a*, 150*b*, 170*a*, and 170*b* respectively. The void areas are sealed off from the cavity such that thermal fluid is prevented from entering the void areas. That reduces the overall volume of the fluid that the wrap accommodates. However, it is beneficial to keep the void areas (rather than simply removing them from the wrap) because overlapping the void areas when the wrap is folded provides connection points to maintain the wrap in a three-dimensional cap form. Preferably, the void areas are provided with hook and loop fasteners such that 152*a* may be folded over 160*a*. The interior of 152*a* may secured to the exterior of 160*a* by hook and loop fasteners. 172*a* may be folded over 152*a* and the interior of 172*a* may be secured to the exterior of 152*a* by hook and loop fasteners. Alternatively, 172*a* could be folded first and 152*a* could be folded over 172*a*. In one embodiment, the exterior of the wrap (or portions of the exterior) is covered with a material of sufficient nap to engage a hook portion of a hook and loop fastener. The cross-hatch portions shown in FIG. 1B may include hooks. The wrap may then be folded over itself as shown in FIGS. 6 and 7 such that the hooks engage the nap of the exterior and hold the wrap in the shape shown in FIG. 6.

Figure 2A:
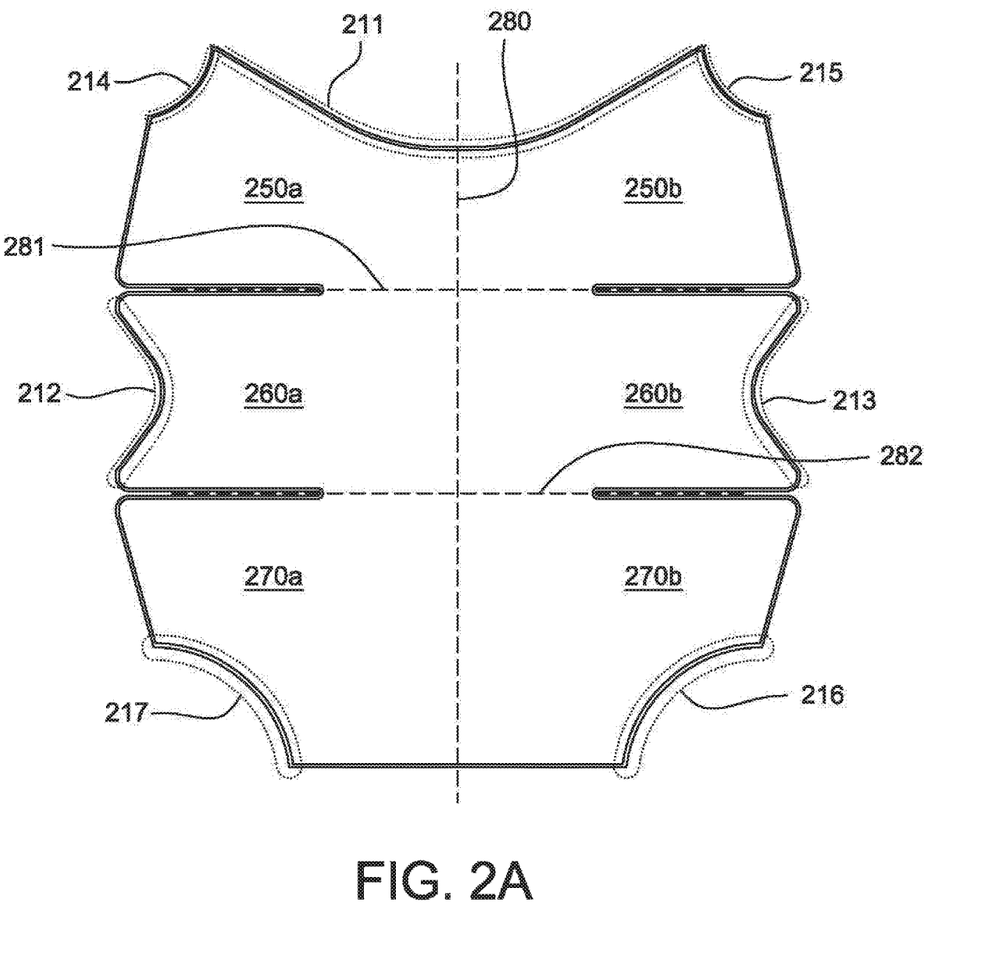
FIG. 2A is a plan view of an embodiment of a wrap laid flat.
Figure 2B:
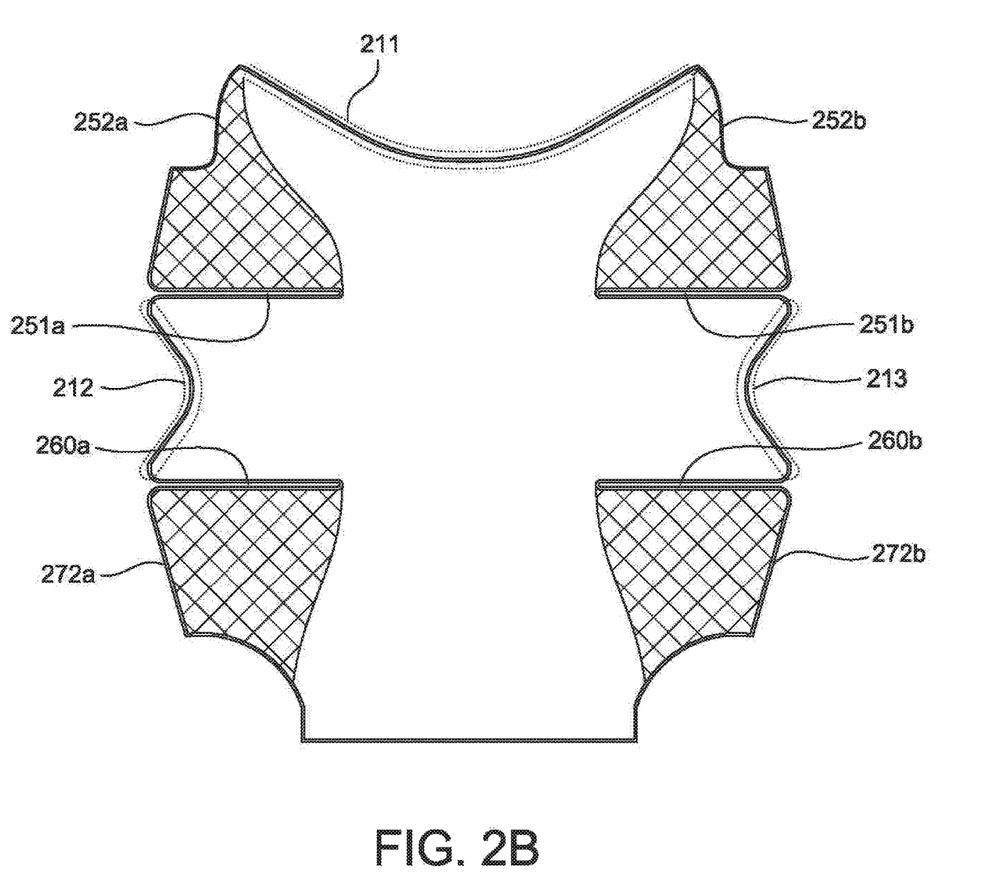
FIG. 2B is plan view of an embodiment of a wrap laid flat and depicting void areas.

FIGS. 2A-2B depict examples of an alternative embodiment. The wrap further includes seals 211, 212, 213, 214, 215, 216, and 217. Seal 211 is adapted to mimic the hairline above the forehead while seals 212 and 213 accommodate the tops of the ears similar to the related seals in FIG. 1B. However, in the embodiment of FIG. 2A, lobes 250*a*, 250*b*, 270*a*, and 270*b* include scallop seals 214, 215, 217, and 216, respectively. The scallop seals further accommodate a person's ears when the wrap is folded into its three-dimensional shape. The scallop seals 214, 215, 217, and 216 approximate the curvature of seals 212 and 213 so as to guide the user into proper alignment of the lobes when folding the wrap.

In each of the wraps, the front lobes are shorter in length than the back lobes. That is because the back lobes are designed to reach down to the nape of the neck where maintenance of hair growth is desired, while the front lobes are designed to traverse the hairline while avoiding the majority of the forehead region. Thus, as shown in FIG. 1B, $L_1$ is less than $L_2$.

The wraps may further be provided with one or more internal pathway seals that are formed by sealing the layers together. The pathway seals can help ensure that fluid is circulated through the wrap rather than simply entering the wrap from hose 192 and immediately exiting the wrap through hose 191. The wraps may also be provided with a plurality of additional pattern seals. Individual seals make up the overall pattern. Each seal has a seal area which is the area defined by the perimeter of the seal within which fluid is prevented from flowing. It should be appreciated that seals that are designed to be the same size might vary slightly in actual dimensions due to variances in the manufacturing process, but will be of substantially the same size and appear to be of the same size. The pattern seals are arranged to maximize fluid flow in particular areas of the wrap, prevent the wrap from kinking and shutting off fluid flow while simultaneously limiting the internal volume of the wrap and preventing the wrap from ballooning.

Figure 3:
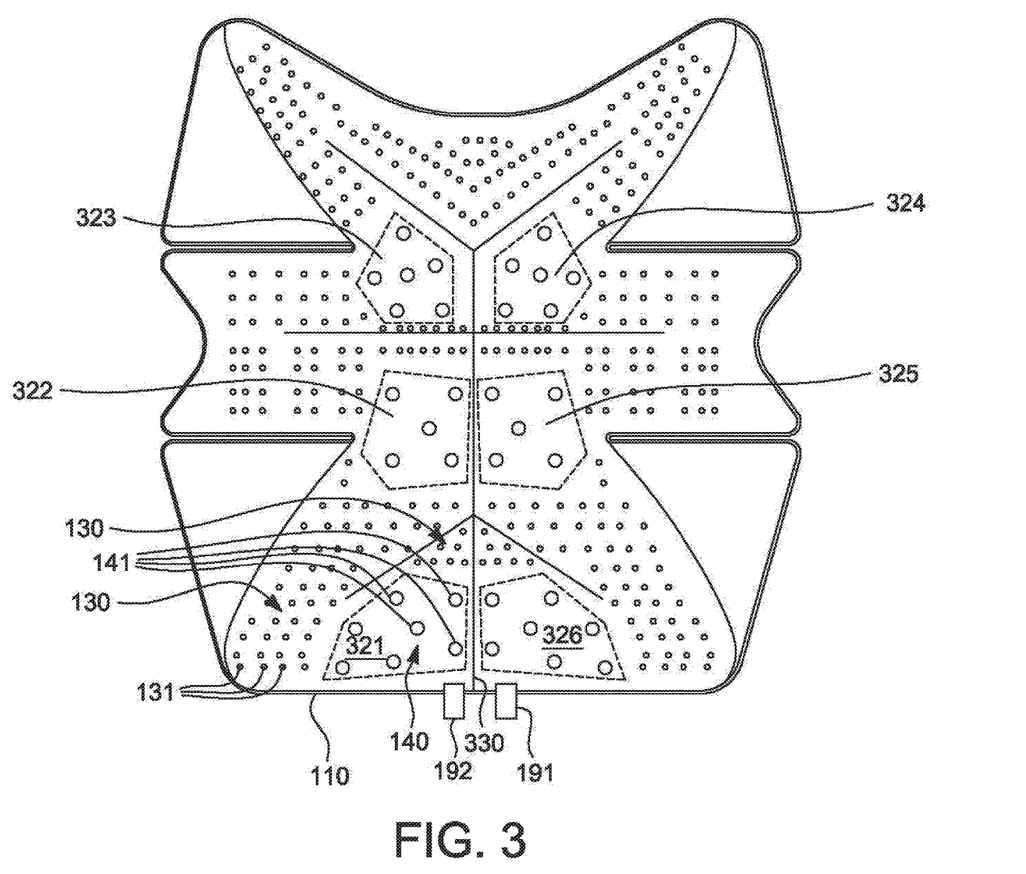
FIG. 3 is a plan view of an embodiment of a wrap depicting pattern zones.

To accomplish the foregoing, a first pattern having relatively large dimensions is provided in at least one zone. A zone is an area of the wrap that has a perimeter defined by either a seal, such as seal 153, 154, 155, 156 or perimeter seal 110, or another pattern or patterns that differ from the pattern in the zone, or a combination of one or more differing patterns formed by dots and one or more seals. For example, the wrap in FIG. 3 has six zones, 321, 322, 323, 324, 325 and 326, each surrounded by a dashed line for explanative purposes. Looking at zone 321, it contains a pattern 140 and it is bordered by perimeter seal 110, internal seal 330, and two sections of pattern 130. As shown in FIG. 3, pattern 130 is different from pattern 140. Preferably, pattern 130 has smaller dimensions than pattern 140. As is shown, pattern 140 includes a number of circular seals, generally referred to by numeral 141, while pattern 130 includes a number of simple dot seals, generally referred to as 131. Additionally, it is preferable that the distances between any two adjacent dot seals 131 that boarder the pattern in a zone (such as zone 312) are each less than related distances between adjacent pattern seals 141 within the zone. Positioning the seals in that manner ensures that the pathways created between the seals 141 accommodate a greater volume of fluid than the pathways between seals 131 such that the zone 321 provides for greater fluid flow than a similar sized area having the alternate pattern 130. It is preferred that the surface area of the cavity defining the zones constitutes a minority of the surface area of the overall cavity while the surface area of the cavity containing the one or more patterns differing from the pattern or patterns contained within the zones constitutes the majority of the surface area of the overall cavity. As shown in FIG. 3, the surface area of the patterned zones 321, 322, 323, 324, 325, and 326, collectively, is less than the surface area of the portions of the wrap containing dot seals 131. The smaller dot seals reduce inflation of the wrap and help conform to the sides of the head while the larger zones are located at the curving dome of the crown of the head to provide greater cooling capacity in that region and weight the wrap down on the top of the head.

It should be recognized that while the particular shapes of the seals 131 and 141 are shown as dots and circles, respectively, they are not limited to those shapes. Circular seals are shown for explanative purposes only and represent only a simple shape, easily formed in the material forming the layers of the wrap. Circular patterns also ensure uniform displacement of wrap layer material during the sealing process and help ensure that pressure points are not formed in the seals. Pressure points tend to occur at sharp edges. When the wrap fills with fluid, the wrap layers tend to pull apart at the sharp edge creates a pressure point that can tear the layers of material. Consequently, while any shape of pattern seal could be used, it is preferred that the pattern seal be provided with a smoothly curved perimeter, such as a circle or oval.

In the embodiment of the wrap shown in FIG. 3, the zones 321, 322, 323, 324, 325, and 326 are located at particular problem areas. Zones 321 and 326 are provided at the inlet and outlet hoses 192 and 191. Placement around the hoses ensures that fluid flow is will not be interrupted as fluid enters and exits the wrap. Zones 322, 323, 324, and 325 are placed in the approximate location where the wrap is designed to fold when it is placed on a person's head. The larger pattern zones will maintain fluid flow through those areas and prevent the wrap from kinking as lobes 150a, 150b, 170a, and 170b are folded over lobes 160a and 160b.

Figure 4:
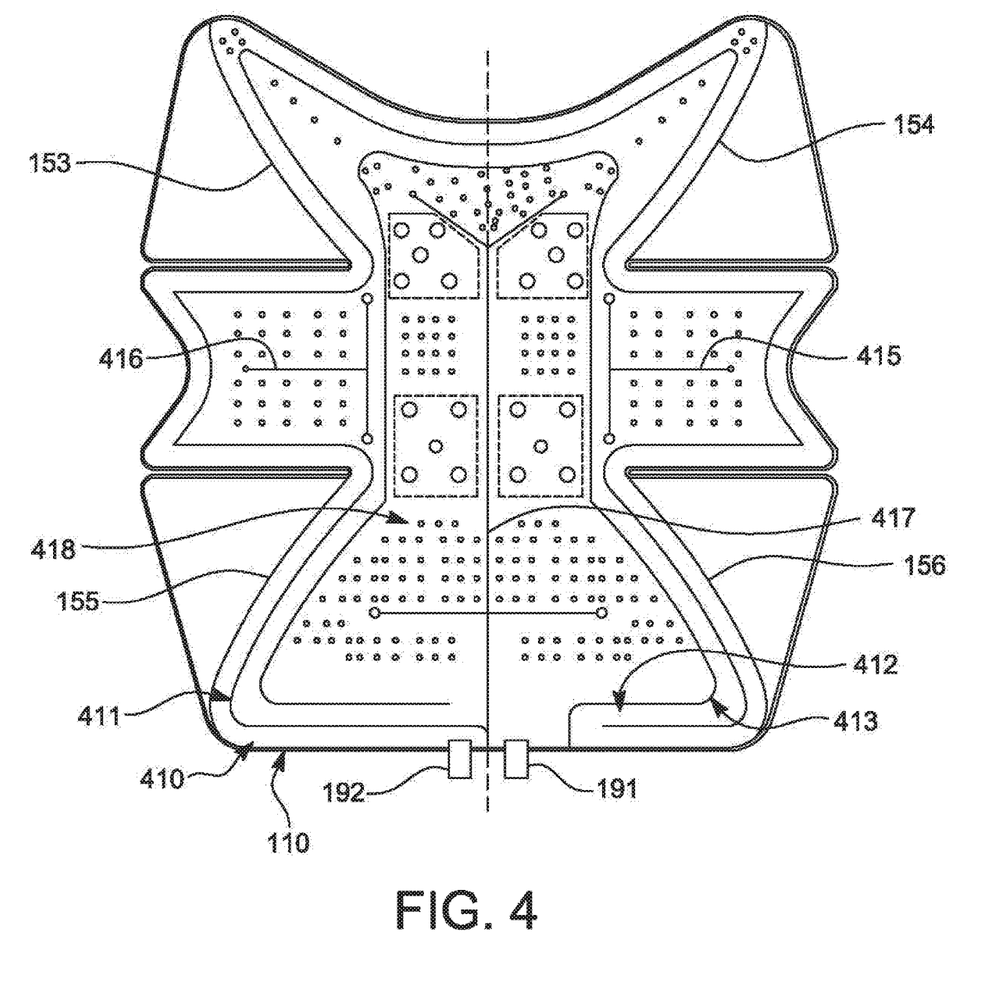
FIG. 4 is a plan view of an embodiment of a wrap depicting circumferential pathways and pattern zones.

An alternative embodiment of a wrap with a differing flow path is depicted in FIG. 4. In that embodiment, fluid enters through tube 192 and is routed into circumferential pathway 410. Circumferential pathway 410 is formed by pathway seal 411 and (as the pathway progresses around the wrap) the perimeter seal 110 and various cavity seals 155, 153, 154, and 156. The circumferential pathway ensures that fluid first entering the wrap completely encircles the wearer's head (except for a negligible short distance surrounding the exit tube 191) before filling the remainder of the wrap. In that way, pressure is applied circumferentially around the patient's head initially to cinch the wrap to the head. It likewise helps evenly distribute weight of the fluid around the head as the wrap fills and avoids having the wrap fill, for example, in the back first which could cause wrap to slip backward.

In the embodiment of FIG. 4, the circumferential pathway 410 leads into a second circumferential pathway 412 bounded by seal 411 and seal 413 that fills the wrap in the opposite direction from pathway 410. That further focuses the fluid on surrounding the patients head, distributing the weight of the fluid and cinching the wrap around the head. Pathway 412 opens as it reaches the side lobes 160b and 160a. That diverts fluid into the side lobes to fill those lobes before the balance of the wrap. Each lobe contains a T shaped internal seal, 415, 416 respectively. The T shape permits fluid to continue to progress past the lobe and through the pathway 412 while the lobe simultaneously fills with fluid. Thus, the second circumferential pathway is separated from the perimeter of the wrap by the first circumferential pathway.

Upon exiting the pathway 412, the fluid is routed along centerline seal 417 which essentially bisects the wrap and maintains separation between hose 192 and 191. The centerline pathway 418 (which is essentially a third, interior pathway separated from the first circumferential pathway by the second circumferential pathway) is wider than the circumferential pathways 410 and 412 and it allows for fluid to fill the balance of the wrap. To maintain uniformity, lobes 160a, 160b, and the centerline pathway 418 may further include dot seals or pattern seals. In the embodiment of FIG. 4, pattern zones are formed where the wrap tends to fold while dot seals fill the balance of the wrap to even the distribution of fluid. It should be appreciated that while the seals and dots have been described with relation to one embodiment, the alternative embodiments could be provided with similarly formed pathways and seals. Also, depending on the size of circumferential pathways 410, 412, dots may also be included in the pathways. However, by keeping the pathways relatively open and free from dots, the fluid tends to more easily traverse the circumferential pathways and allows the pathways to better expand and cinch to the patient's head. For example, in one embodiment, the outer layer of the wrap is less elastic than the inside layer (which contacts the scalp). As fluid is forced into the wrap, the pressure against the layers increases. However, the more elastic inside layer tends to balloon more than the relatively inelastic outer layer. Therefore the inner layer expands to press against the patients head and create compression as the inner layer is restricted from expanding outward by the more inelastic outer layer.

Figure 5:
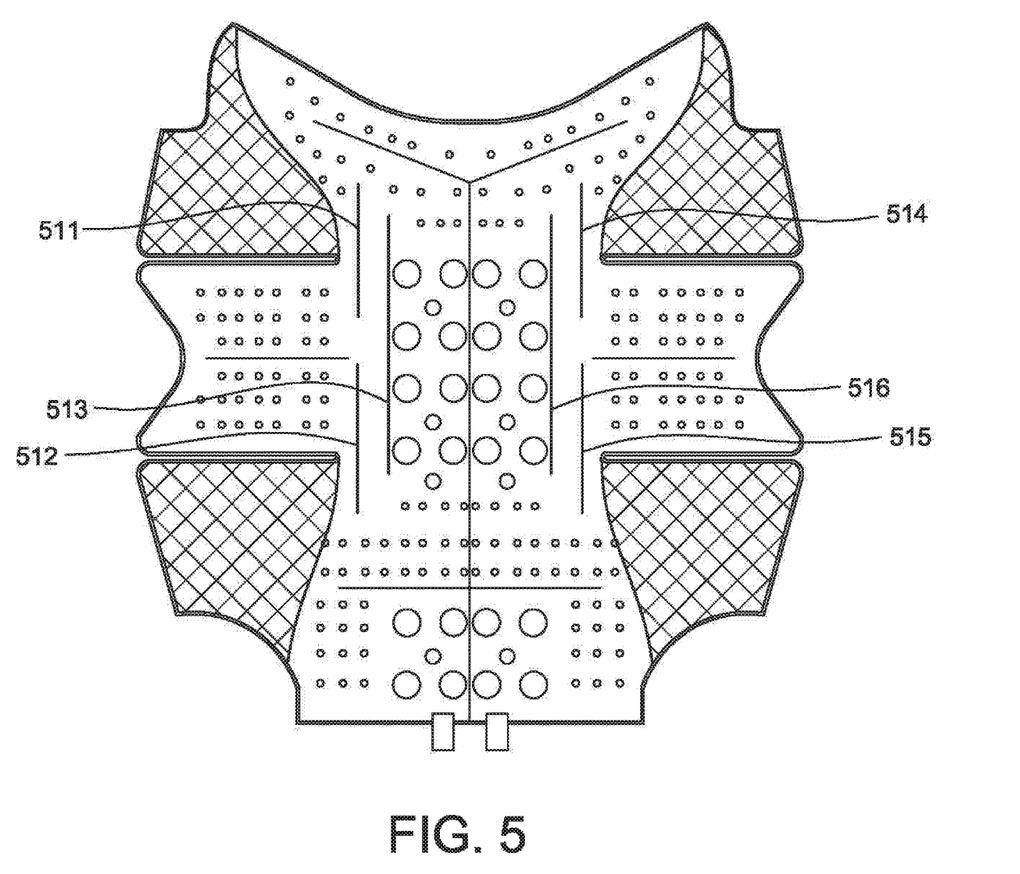
FIG. 5 is a plan view of an embodiment of a wrap depicting rib seals.

Another embodiment with an alternative seal pattern is depicted in FIG. 5. According to that embodiment, seals 511, 512, 513, 514, 515, and 516, are provided. The seals extend over the areas of the wrap that are susceptible to kinking when the wrap is folded. By applying the seals across those areas in a front-to-back manner, the seals help direct fluid flow directionally through the areas where the wrap tends to kink. The seals also assist in having the wrap fold properly. In one embodiment, additional reinforcement may be applied at one or more of the seals 511-516. For example, additional resilient material, such as a semi-rigid, yet flexible and elastic plastic strip, may be applied to the wrap along those seal lines. One manner of constructing such a wrap is to form the wrap as described above, then place the strips in the areas where the seals are desired, add an additional layer of material over the strips, and RF weld the additional layer to the underlying wrap layers so as to encase the strips in pockets of material. As the wrap is folded, the resiliency of the strips assists in forming the wrap to the curvature of the skull while still elastically pushing outward to help open the fluid pathways.

FIGS. 6-7 depict embodiments of the wraps discusses above in a folded state. The void areas are folded over the side lobes and may connect to each other and the side lobes through fasteners (such as hook and loop fasteners) to thereby form a cap. It should be understood that fasteners may be constructed of two halves that are adapted to engage with one another. For example a first half of a Velcro fastener may be loops and a second half of a Velcro fastener may be hooks. For example a first half of a snap may be a male portion and a second half of a snap may be a female portion.

As discussed above, the wraps may be connected to a machine for thermally conditioning a fluid and pumping that fluid through the wrap. For the treatment of hair loss, it has been found that the optimal treatment temperature for the thermal transfer fluid is between 36 degrees and 49 degrees Fahrenheit. The preferred particular temperature may vary depending on the chemotherapy drug being administered to the patient receiving therapy. Additionally, compression of the wrap against the head aids significantly to the effectiveness of the treatment. The present wraps are designed to provide the desired level of compression through forcing fluid through the flowpaths of the wraps and without the need for additional compression pumps (i.e. without the need to inflate additional gas cavities on the outside of the wraps). In operation, when the wrap is connected to a hose which is connected to the pump of a thermal transfer machine (such as that described in U.S. Pat. No. 8,979,915) which cycles the thermal fluid to the wrap. The pressure through the hose and in the wrap increases as the fluid enters the wrap to a preferred therapy pressure of approximately 10 to 15 mmHg.

In one embodiment, the nominal flow rate of the fluid pump of the fluid transfer machine is approximately 0.65 Liters/minute (LPM). The approximate total water volume held within the reservoir of fluid transfer machine, internal plumbing, and hoses connecting to a wrap may be approximately 0.4 to 0.6 Liters, or an average of 0.5 Liters. Where no wrap is connected to the fluid transfer system, the approximate time to circulates the water may be determined as Time (minutes)=Total Volume/Flow Rate=0.5 L/0.65 LPM=0.77 min (or about 45 seconds). If a filled wrap is connected, the volume of the wrap is added to the total volume and the time to circulate is recalculated. For example: Time with wrap (min)=(0.5 L+Wrap Vol in Liters)/0.65 LPM. In one embodiment, the present wrap holds approximately 0.2 L. Thus the circulation time is approximately (0.5+0.2)/0.65=1.07 min (or 1 min, 4 seconds). By minimizing the fluid in the system, it is possible to quickly circulate the fluid through the system such that the temperature of the fluid remains adequately stable, and the size of the thermal transfer machine can remain portable so as to allow a patient to carry the machine wile simultaneously receiving treatment.

Thus the present system may provide a method of thermal therapy for the prevention of hair loss. To mitigate hair loss, such as during chemotherapy, a patient applies the head wrap by securing (such as by Velcro) lobe 150*a* and 170*a* over 160*a* and similarly 150*b* and 170*b* over 160*b*. The thermal transfer unit is connected to the wrap and thermally treats a thermal transfer fluid in a reservoir. The thermal transfer machine pumps fluid through the fluid circuit formed by the fluid transfer unit and the wrap, preferably at total volume transfer time of approximately 45 seconds to a minute while maintaining a temperature between 36 degrees and 49 degrees Fahrenheit.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A thermal wrap comprising:
   at least two layers of material sealed together about a perimeter seal to form a cavity there between, where the perimeter seal defines the exterior shape of the wrap such that the wrap is formed of a top section, middle section, and bottom section;
   the top section is connected to the middle section;
   the bottom section is connected to the middle section such that the middle section is disposed between the top section and bottom section;
   the top section is comprised of two lobes having substantially the same shape that are connected together along a vertical central axis line that forms a line of symmetry between a right half of the wrap and a left half of the wrap and wherein a top perimeter portion of the top section is formed in a concave parabolic curve that is symmetrical about the vertical central axis such that a trough of the curve is positioned toward a vertical center point of the wrap;
   the middle section is comprised of two lobes having substantially the same shape that are connected together along the vertical central axis line; and
   the bottom section is comprised of two lobes having substantially the same shape that are connected together along the vertical central axis line.

2. The thermal wrap as in claim 1, wherein the shape of the right half of the wrap is symmetrical to the shape of the left half of the wrap about the vertical central axis line.

3. The thermal wrap as in claim 1, wherein a first lobe of the middle section is partially separated from a first lobe of the top section by a first slit;
   the first lobe of the middle section is partially separated from a first lobe of the bottom section by a second slit;
   a second lobe of the middle section is partially separated from a second lobe of the top section by a third slit; and
   the second lobe of the middle section is partially separated from a second lobe of the bottom section by a fourth slit.

4. The thermal wrap as in claim 3 wherein each slit is substantially perpendicular to the vertical central axis line.

5. The thermal wrap as in claim 3 wherein a portion of the perimeter of the first lobe of the middle section that connects the first slit and second slit exhibits a concave parabolic curve, where a trough of the curve is disposed toward the vertical central axis line.

6. The thermal wrap as in claim 3 wherein the two lobes of the bottom section form a substantially trapezoidal shape that is symmetrical about the vertical central axis line.

7. The thermal wrap as in claim 6 wherein a portion of the perimeter of the first lobe of the middle section that connects the first slit and second slit exhibits a concave parabolic curve having a trough that is disposed toward the vertical central axis line.

8. The thermal wrap as in claim 6 wherein a vertical length of the top section measured from the upper most portion of the perimeter of the top section vertically down to the first slit is less that a vertical length of the bottom section measured from the lower most portion of the perimeter of the bottom section vertically up to the second slit.

9. The thermal wrap as in claim 3 further comprising:
a plurality of pattern zones formed of seals between the at least two layers of material, wherein the plurality of pattern zones further comprises:
a first pattern zone disposed entirely within the first lobe of the bottom section;
a second pattern zone disposed entirely within the second lobe of the bottom section;
a third pattern zone disposed partially within the first lobe of the bottom section and partially within the first lobe of the middle section; a fourth pattern zone disposed partially within the second lobe of the bottom section and partially within the second lobe of the middle section;
a fifth pattern zone disposed partially within the first lobe of the middle section and the first lobe of the top section; and
a sixth pattern zone disposed partially within the second lobe of the middle section and the second lobe of the top section.

10. The thermal wrap as in claim 3 further comprising: a plurality of pathway seals that define a circuitous fluid pathway between an ingress tube disposed in the first lobe of the bottom section and an egress tube disposed in the second lobe of the bottom section such that a fluid flowing from the ingress tube to the egress tube is forced through the cavity in the following order:
a) entering a first circumferential pathway and flowing first along a portion of the perimeter defining the first lobe of the bottom section;
b) then along a portion of the perimeter defining the first lobe of the middle section;
c) then along a portion of the perimeter defining the first lobe of the top section;
d) then along a portion of the perimeter defining the second lobe of the top section;
e) then along a portion of the perimeter defining the second lobe of the middle section;
f) then along a portion of the perimeter defining the second lobe of the bottom section;
g) entering a second circumferential pathway and flowing then along an interior portion of the second lobe of the bottom portion;
h) then along an interior portion of the second lobe of the middle portion;
i) then along an interior portion of the second lobe of the top portion;
j) then along an interior portion of the first lobe of the top portion;
k) then along an interior portion of the first lobe of the middle portion;
l) then along an interior portion of the first lobe of the bottom portion;
all before entering a third fluid pathway and flowing through a central portion of the cavity and out the egress tube.

11. The thermal wrap as in claim 10 wherein the second circumferential pathway is separated from the perimeter of the wrap by the first circumferential pathway.

12. The thermal wrap as in claim 10 wherein the second circumferential pathway is separated from the perimeter of the wrap by the first circumferential pathway.

13. The thermal wrap as in claim 1 further a first cavity restricting seal extending from the perimeter seal to a first slit, a second cavity seal extending from the perimeter seal to a second slit, a third cavity restricting seal extending from the perimeter seal to a third slit, and a fourth cavity restricting seal extending from the perimeter seal to a fourth slit.

14. The thermal wrap as in claim 13, wherein the first, second, third, and fourth cavity restricting seals in conjunction with portions of the perimeter seal defining edges of each lobe form a cavity that is substantially symmetrical about the vertical central axis.

15. The thermal wrap as in claim 14 wherein an ingress tube is provided in a first lobe of the bottom section and an egress tube is provided in a second lobe of the bottom section.

16. A thermal wrap comprising:
at least two layers of material sealed together about a perimeter seal to form a cavity there between, where the perimeter seal defines the exterior shape of the wrap such that the wrap is formed of a top section, middle section, and bottom section and such that the wrap has a front side and a back side opposite the font side;
the top section is connected to the middle section;
the bottom section is connected to the middle section such that the middle section is disposed between the top section and bottom section;
the top section is comprised of two lobes, each lobe being disposed on opposite sides of a vertical central axis of the wrap;
the middle section is comprised of two lobes, each lobe being disposed on opposite sides of a vertical central axis of the wrap; and
the bottom section is comprised of two lobes, each lobe being disposed on opposite sides of a vertical central axis of the wrap;
wherein, the front side of one of the lobes of the bottom section on a first side of the vertical central axis includes one half of a fastener;
wherein the back side of one of the lobes of the middle section on the first side of the vertical central axis include one half of a fastener;
wherein the front side of one of the lobes of the top section includes one half of a fastener; and
wherein at least the half of the fastener on the front side of the lobe of top section or the half of the fastener on the front side of the lobe of the bottom section is adapted to fasten to the one half of the fastener on the back side of the lobe of the middle section.

17. The thermal wrap as in claim 16 wherein at least one of the one half of the fastener on either the front side of lobe of the bottom section or on the front side of the lobes of the top section is either the hook portion or the loop portion of a hook and loop fastener, and wherein the one half of the fastener on the back side of the lobes of the middle section is the complementary hook portion or loop portion of a hook and loop fastener.

18. The thermal wrap as in claim 16 wherein a lobe of the top section is disposed on a second side of the vertical central axis, a lobe of the middle section is disposed on the second side of the vertical central axis, and a lobe of the bottom section is disposed on the second side of the vertical central axis;
wherein each of the lobes on the second side of the vertical central axis include one half of a fastener;

wherein the halves of the fastener on each lobe of the top section are the same type such that the halves are not adapted to connect to one another;

wherein the halves of the fastener on each lobe of the middle section are the same type such that the halves are not adapted to connect to one another; and wherein the halves of the fastener on each lobe of the bottom section are the same type such that the halves are not adapted to connect to one another.

19. A thermal wrap comprising:

at least two layers of material sealed together about a perimeter seal to form a cavity there between, where the perimeter seal defines the exterior shape of the wrap such that the wrap is formed of a top section, middle section, and bottom section;

the top section is connected to the middle section;

the bottom section is connected to the middle section such that the middle section is disposed between the top section and bottom section;

the top section is comprised of two lobes having substantially the same shape that are connected together along a vertical central axis line that forms a line of symmetry between a right half of the wrap and a left half of the wrap;

the middle section is comprised of two lobes having substantially the same shape that are connected together along the vertical central axis line;

the bottom section is comprised of two lobes having substantially the same shape that are connected together along the vertical central axis line;

wherein a first lobe of the middle section is partially separated from a first lobe of the top section by a first slit;

the first lobe of the middle section is partially separated from a first lobe of the bottom section by a second slit;

a second lobe of the middle section is partially separated from a second lobe of the top section by a third slit;

the second lobe of the middle section is partially separated from a second lobe of the bottom section by a fourth slit; and the wrap further comprising:

a plurality of pathway seals that define a circuitous fluid pathway between an ingress tube disposed in the first lobe of the bottom section and an egress tube disposed in the second lobe of the bottom section such that a fluid flowing from the ingress tube to the egress tube is forced through the cavity in the following order:

a) entering a first circumferential pathway and flowing first along a portion of the perimeter defining the first lobe of the bottom section;

b) then along a portion of the perimeter defining the first lobe of the middle section;

c) then along a portion of the perimeter defining the first lobe of the top section;

d) then along a portion of the perimeter defining the second lobe of the top section;

e) then along a portion of the perimeter defining the second lobe of the middle section;

f) then along a portion of the perimeter defining the second lobe of the bottom section;

g) entering a second circumferential pathway and flowing then along an interior portion of the second lobe of the bottom portion;

h) then along an interior portion of the second lobe of the middle portion;

i) then along an interior portion of the second lobe of the top portion;

j) then along an interior portion of the first lobe of the top portion;

k) then along an interior portion of the first lobe of the middle portion;

l) then along an interior portion of the first lobe of the bottom portion;

all before entering a third fluid pathway and flowing through a central portion of the cavity and out the egress tube.

\* \* \* \* \*